(12) United States Patent
Petta

(10) Patent No.: US 6,401,055 B1
(45) Date of Patent: Jun. 4, 2002

(54) METHOD AND SYSTEM OF MEASURING AND QUANTIFYING INEFFICIENCIES IN A HEALTHCARE FACILITY

(75) Inventor: John Joseph Petta, Waukesha, WI (US)

(73) Assignee: General Electric Company, Inc., Schenectady, NY (US)

( * ) Notice: Subject to any disclaimer, the term of this patent is extended or adjusted under 35 U.S.C. 154(b) by 0 days.

(21) Appl. No.: 09/430,569

(22) Filed: Oct. 29, 1999

(51) Int. Cl.$^7$ .............................................. G06F 17/60
(52) U.S. Cl. ............................. 702/182; 705/2; 705/5; 600/407
(58) Field of Search ................................ 702/182, 179; 705/2, 3, 4; 600/407, 425; 208/162

(56) References Cited

U.S. PATENT DOCUMENTS 6,282,513 B1 * 8/2001 Strawder ....................... 705/2

* cited by examiner

Primary Examiner—Kamini Shah
(74) Attorney, Agent, or Firm—Michael Best & Friedrich LLP

(57) ABSTRACT

A method and system for measuring and quantifying inefficiencies in a medical procedure such as a radiological procedure. Inefficiencies are measured and quantified by collecting a plurality of characterization measurements, where each characterization measurement corresponds to an individual step in the procedure. Once the measurements are collected, a sum of squares analysis is performed on them to determine the effect of each step on the procedure. The process steps are further analyzed to determine the activities within them that have the highest impact on the time needed to complete the task or tasks that make up the step. These tasks or key drivers are then subjected to a regression analysis to determine their effect on the time to complete the procedure. The key drivers may then be changed to adjust the procedure as desired.

17 Claims, 2 Drawing Sheets

METHOD AND SYSTEM OF MEASURING AND QUANTIFYING INEFFICIENCIES IN A HEALTHCARE FACILITY

BACKGROUND OF THE INVENTION

The present invention relates to methods and systems for improving the performance of a department in a healthcare facility. More specifically, the present invention relates to a method of evaluating and reducing inefficiencies in the department.

Healthcare facilities such as hospitals and clinics are generally organized in departments specializing in specific areas of medical science such as immunology, cardiology, and radiology. Generally, specialized personnel and equipment are available in each department to provide medical treatment in the area of specialization. Often times, these departments must repeatedly perform the same or similar procedures on many patients. By way of example, radiology departments often carry out many similar procedures using radiant energy to diagnose and treat disease. One well-known use of radiation is in the creation of radiographs that are used to evaluate injuries such as bone fractures.

In general, before a specialized procedure is performed in a department of a healthcare facility, a patient is evaluated by a physician that typically does not specialize in the medical area covered by the relevant department (the "referring physician"). Once the referring physician has determined that a specialized procedure would facilitate the diagnosis or treatment of the patient, the patient is sent to the applicable department and the staff there conducts the requested procedure.

While the above description makes the process seem simple, examining a patient can be logistically complex and involve many steps. Using a radiological procedure as an example, following his or her initial examination, a patient must schedule an appointment for the radiological examination. Then, the patient must travel to the department at the appointed time and date. Upon arrival at the radiology department the patient registers with the radiology staff and is prepared for the radiological examination, if necessary, such as by donning an examination gown. The patient may then have to wait until an examining room is available and then is examined. Following the examination, the radiograph or other imagery must be examined by a radiologist. Finally, the radiologist prepares a report which is then sent to the referring physician.

The competence and efficiency with which each of these tasks is conducted affects the overall quality and efficiency of the radiology department. It also affects the patient's and referring physician's satisfaction with the services performed. Thus, to the extent that efficiency and satisfaction could be improved, the operation of the department, including such things as quality and profitability, could also likely be improved. Yet, scientific and other structured methodologies have not, in general, been applied to study and improve the operations of a radiology department or, for that matter, other procedures that are carried out on a relatively frequent basis in the departments of a healthcare facility. Accordingly, there is a need for a method or system of evaluating and improving the operations of a department in a healthcare facility.

SUMMARY OF THE INVENTION

Therefore, the present invention provides a method and system for measuring and quantifying inefficiencies in the operations of a department in a healthcare facility. The method and system are useful in identifying the root causes of inefficient operation of the department so that change can be effected that improves the operation of the department.

The method includes the acts of collecting a plurality of characterization measurements for a medical procedure, where each characterization measurement corresponds to an individual step in the procedure. The collection of the measurements may be done by a variety of known manual and automated techniques, none of which is critical, by itself, to the invention. Of course, like any measurement process, accurate measurements are desirable. Once the measurements are collected, a sum of squares analysis is performed on the measurements to determine the effect of each step on the examination procedure. Further analysis is conducted to determine the activities within each process step that have the highest impact on the time needed to complete the subject task that makes up the step. These activities are known as the key drivers. A regression analysis is then performed on the key drivers to determine the effect of the key drivers on the overall time to complete the procedure. The key drivers are then changed to adjust the procedure as desired.

It is an advantage of the present invention to provide a structured analysis of medical procedures conducted in a healthcare facility. As a part of the analysis, key root causes for inefficiency are found and analyzed appropriately. Another advantage of the present invention is that the procedure may be modified to reduce or eliminate the identified causes of inefficiency. This results in procedures that may be accomplished in less time and with less resources than previously obtainable. The reduction in time leads to shorter completion times and faster diagnoses and treatments. The reduction in resources leads to enhanced profitability and lower prices.

Other features and advantages of the present invention will become apparent by consideration of the detailed description and accompanying drawings.

DETAILED DESCRIPTION

Figure 1:
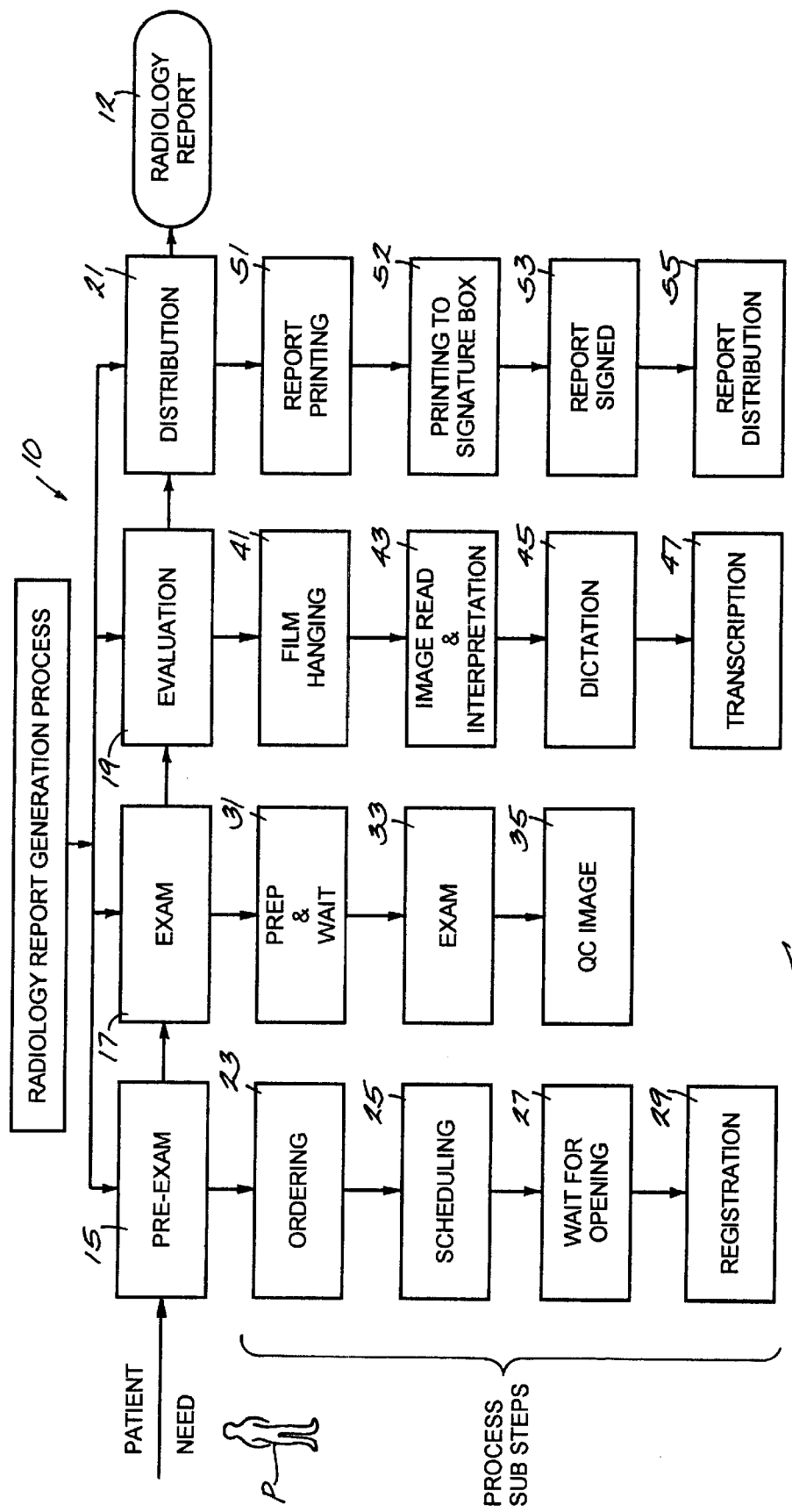
FIG. 1 is a flow chart illustrating the general process of producing a report for a radiological examination conducted on a patient in a radiology department.

As noted above, scientific and other structured methodologies have not, in general, been applied to improving medical procedures. The inventor has discovered that by conducting certain statistical analyses on medical procedures, inefficiencies in those procedures may be identified. Further, once those inefficiencies are identified, improvements to the process may be made. While it is assumed that the reader understands statistical methods, before discussing the particular aspects of the present invention, a brief summary of the statistical methods used is in order.

Analysis of variances (known as "ANOVA") is a statistical methodology used to test hypotheses about differences between two or more means (intermediate values). For example, suppose a researcher has performed a study on various methods of caring for plants; methods A, B, C, and D, with a control group E. Suppose, again, that the goal of the study is to determine if one method is more effective than the others and, for purposes of this example, assume that twenty plants are assigned to each group. At the end of the study, changes in health were found for each plant. However, how does the researcher compare the means of each of the groups in order to make a determination as to the effectiveness of the methods? One way would be to individually compare each group to all the others. For the present example, this would require ten comparisons. Using ANOVA, the number of comparisons may be reduced.

Without explaining the entire underlying theory, ANOVA relies on statistical sampling. A sample is a finite number (N) of scores and those scores may be interpreted through such statistics as the mean (x), the mode ($M_o$), the median ($M_d$) and standard deviation ($s_x$). The sample statistics may then be used as estimators of the corresponding parameters in the population model. A sampling distribution may then be found to further analyze the sample statistics. Ultimately, the variance of a population and a measure of how different the means are relative to the variability within each sample may be used to determine the likelihood that the differences between the means of each group are due to chance rather than real effects. ANOVA analyses may be conducted using commercially available software.

Before one embodiment of the invention is explained in detail, it is to be understood that the invention is not limited in its application to the details of construction and to the arrangements of components set forth in the following description or illustrated in the drawings. The invention is capable of other embodiments and is capable of being practiced or of being carried out in various ways. Also, it is to be understood that the phraseology and terminology used herein is for the purpose of description and should not be regarded as limiting.

FIG. 1 schematically illustrates a radiological examination procedure 10 resulting in the generation of a radiological report 12. (It should be understood, that the radiological procedure 10 is used as an exemplary medical procedure and that the teachings of the present invention are applicable to other procedures.) As noted above, once a determination is made that a patient needs or requires a radiological procedure, the patient (represented by the patient P) interacts with a radiology department with the final result of producing a radiological report. The procedure 10 may be conceptualized as having four major steps: a pre-examination step 15; a main examination step 17; an evaluation step 19; and a distribution step 21. The pre-examination step 15 involves several sub-steps: ordering the radiological procedure 23, scheduling the procedure 25, waiting for the examination 27, and registration 29. Once ordered and scheduled, the actual examination or procedure is conducted. The main examination step 17 includes a period of patient preparation and waiting 31, an actual examination period 33, and quality control review 35 of the image made during the examination. Once an image of sufficient quality has been produced, it must be evaluated by a radiologist. The evaluation step 19 requires image hanging or display 41 and review and interpretation 43 of the image. Generally, as the radiologist reviews the image he or she dictates an oral report on the results of the radiological procedure as represented by a dictation sub-step 45. The final step in evaluation of the examination is a transcription sub-step 47 where the dictated report is transcribed to a form that may be printed.

Once the report is transcribed, it is distributed. The distribution step 21 involves a report printing sub-step 51, a printing to signature box sub-step 52 during which the printed report is transferred to a signature box, a signing of the report sub-step 53, and an actual distribution of the report sub-step 55, where the report is sent to the referring physician, the patient, or both. The radiology examination process as shown in FIG. 1, is represented in a process map shown below in Table 1. Each process step has a corresponding characterization measurement. In other words, each process step may be considered as representing a characterization measurement.

TABLE 1

| STEP SEQUENCE NUMBER | PROCESS STEP | CHARACTERIZATION MEASUREMENT |
|---|---|---|
| 1 | Ordering of the radiological procedure 23 | Military hour of day call comes from referring physician to radiology department at hospital or other facility. |
| 2 | Scheduling of procedure 25 | Time of scheduled exam. |
| 3 | Waiting for examination 27 | Elapsed time between referring physician call and scheduled exam time. |
| 4 | Registration 29 | Elapsed time between patient arrival at registration desk of facility and patient arrival in radiology department. |
| 5 | Patient preparation and waiting 31 | Elapsed time between moment patient arrives in radiology department and the moment patient called for examination. |
| 6 | Examination period 33 | Elapsed time between moment patient is called for examination and initial image or scanning completion. |
| 7 | Quality control review 35 | Elapsed time between initial image or scanning completion and the moment the image is sent to the review or reading stack. |
| 8 | Image display 41 | Elapsed time between moment the image is sent to the reading stack and the moment it is viewed (put on a view box) by a radiologist. |
| 9 | Review and interpretation of image 43 | Elapsed time from Exam put on view box by radiologist and exam sent for dictation. |
| 10 | Dictation sub step 45 | Elapsed time for dictation of report. |

TABLE 1-continued

| STEP SEQUENCE NUMBER | PROCESS STEP | CHARACTERIZATION MEASUREMENT |
|---|---|---|
| 11 | Transcription 47 | Elapsed time from moment dictated report complete to transcription complete. |
| 12 | Printing 51 | Elapsed time from transcription complete to report sent to printing. |
| 13 | Printing to signature box 52 | Elapsed time from report sent to printing to report put in radiologist's signature box. |
| 14 | Signing of the report 53 | Elapsed time from report put in radiologist's signature box to radiologist signs report. |
| 15 | Actual distribution 55 | Elapsed time from radiologist signs report to report sent for distribution. |

The measurements listed in Table 1 may be made using various known manual and automated statistical collection techniques. By collecting the characterization measurements for each of the plurality of steps in Table 1, a sum of squares in an ANOVA may be used to determine the effect of each step on the examination procedure 10. The result is a model containing the effect each process step has on the overall measurement of the time needed to complete the procedure 10. This time is equivalent to or may be considered to be the report turnaround time ("RTT"). The results of an exemplary ANOVA based on the characterization measurements of Table 1 are shown in Table 2. The ANOVA illustrated was conducted using Minitab™ software.

TABLE 2

| STEP SEQUENCE NUMBER | PROCESS STEP | SUM OF SQUARES | PERCENTAGE OF CONTRIBUTION |
|---|---|---|---|
| 1 | Ordering of the radiological procedure 23 | 14,481,112 | 6.2% |
| 1_1 | Day of the week | | |
| 1_1(a) | Monday | 1,978,734 | 0.8% |
| 1_1(b) | Tuesday | 1,701,501 | 0.7% |
| 1_1(c) | Wednesday | 3,822,467 | 1.6% |
| 1_1(d) | Friday | 7,855,616 | 3.4% |
| 1_1(e) | Sunday | 272,808 | 0.1% |
| 3 | Waiting for examination 27 | 18,058,259 | 7.7% |
| 4 | Registration 29 | 12,783,330 | 5.5% |
| 5 | Patient preparation and waiting 31 | 16,853,469 | 7.2% |
| 6 | Examination period 33 d | 8,288,351 | 3.5% |
| 7 | Quality control review 35 | 13,766,310 | 5.9% |
| 8 | Image display 41 | 10,401,856 | 4.5% |
| 9 | Review and interpretation of image 43 | 17,796,404 | 7.6% |
| 10 | Dictation sub step 45 | 12,519,046 | 5.4% |
| 11 | Transcription 47 | 21,929,350 | 9.4% |
| 12 | Printing 51 | 21,515,497 | 9.2% |
| 13 | Printing to signature box 52 | 9,113,492 | 3.9% |
| 14 | Signing of the report 53 | 16,903,437 | 7.2% |
| 15 | Actual distribution 55 | 23,580,814 | 10.1% |
| | Total | 233,580,814 | 563.2% |

The data in Table 2 reflects the results of the ANOVA analysis modified to accommodate experiences encountered during the measurement process. First, the second sequence step, scheduling a procedure 25, was eliminated because the time to complete the step was found to be insignificant in relative comparison to the times required to complete other tasks. In addition, an additional sequence step, day of the week, was added to the analysis because it was found that the specific day that the exam was ordered or performed affected completion of the procedure. This occurred because staffing levels often varied by the day of the week. In general, the first part of the week was fully staffed where the latter part of the week or "weekend," as used herein, was staffed at lower levels.

Figure 2:
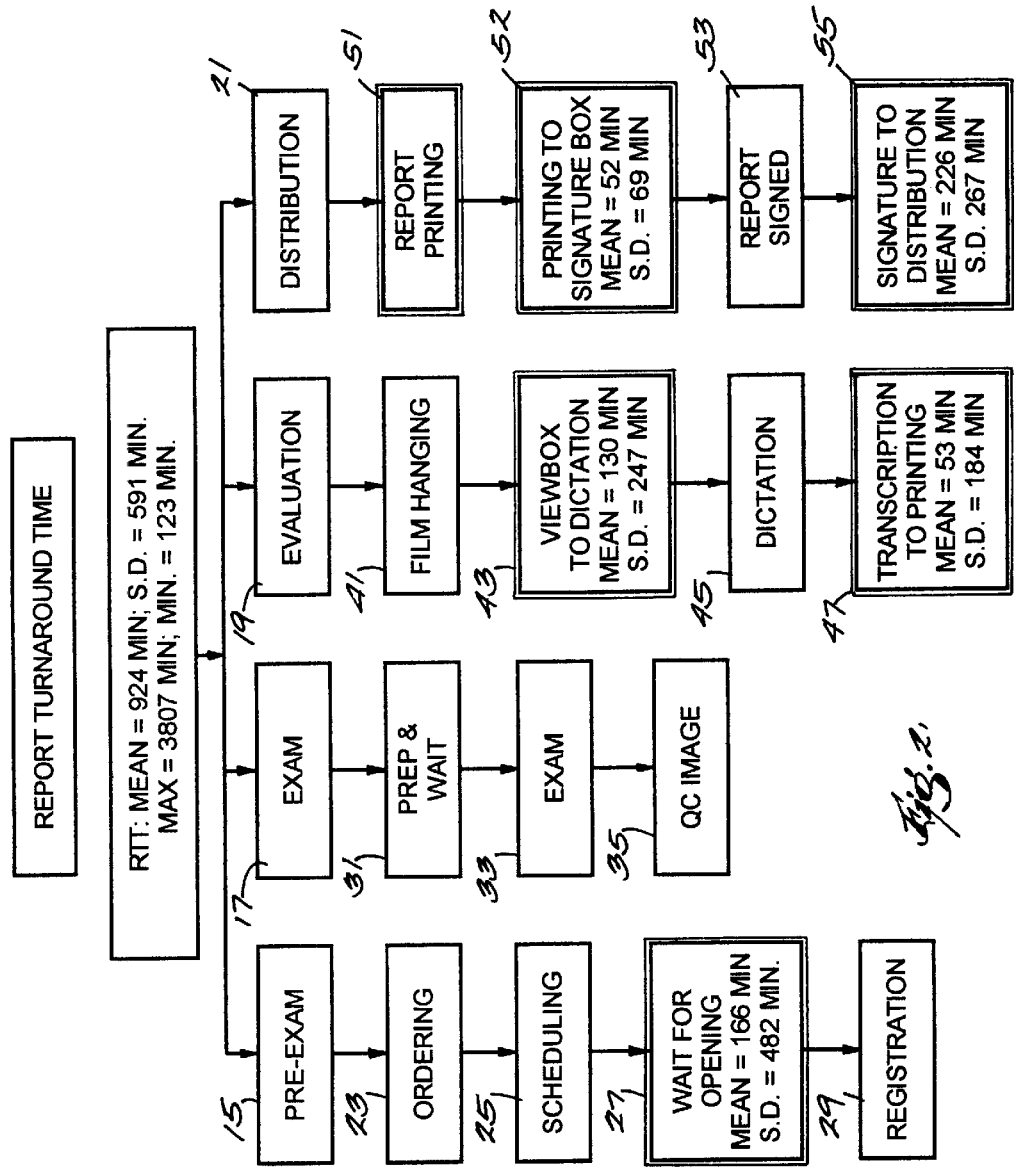
FIG. 2 is a flow chart illustrating the process of producing a report on a radiological examination where steps that heavily impact or drive report turn around time have been identified.

While adding or removing steps based on observations is not required, doing so enhances the accuracy of the analysis. Once the data in Table 2 is obtained, each of the process steps may be further analyzed to determine the activities within each that have the highest impact on the time needed to complete the subject task. In other words, the "key drivers" for each step are determined. As an alternative to analyzing each process step, those process steps having the highest percentage of contribution to the sum of squares total may be identified. Preferably, and as shown in Table 2 and FIG. 2, the top five or six measurements are identified. For the example discussed herein, the top six measurements were waiting for an opening 27, review and interpretation of image 43, transcription 47, printing 51, signing of the report 53, and actual distribution 55.

Once the key drivers are identified, whether derived for all or only a portion of the process steps in the procedure 10, a multiple regression method is used to determine the effect of the key drivers on the overall measurement, i.e., the RTT. The regression analysis performed is consistent with standard regression methods where the dependent variable (in this case, one of the process steps in the procedure) is examined in light of its independent variables (the activities or sub-steps that make up each process step). The correlation between the dependent variable and its independent variables determines which activity or sub-step has the greatest impact on the overall process. As with the ANOVA analysis, the regression analysis may be performed using commercially available software such as the Minitab software noted above. Once the important independent variables or key indicators are found, they are modified to change the larger process as desired. This is best understood by reference to Table 3, below.

TABLE 3

| PROCESS STEP | KEY DRIVER | IMPACT ON RTT |
|---|---|---|
| Waiting for an opening 27 | Problem: Staffing of Technicians Solution: Overlap technicians shifts & match scheduling of examinations to schedule | Decrease RTT variation by 30% and decrease RTT mean by 120 minutes |
| Review and interpretation of image 43 | Problem: Radiologists batching jobs, "overnight" and "weekend" effect Solution: Move to overlapped shifts | Decrease RTT variation by 8% |
| Printing 51 | Problem: Batch printing as a result of radiologists batch work routine. Solution: Printing at end of transcription and transcribing staffing matched to new Radiologists staffing patterns | Decrease RTT variation by 11%, lessen "overnight" & "weekend" effect |
| Signature box 52 | Problem: Batch review and signature of reports Solution: 1) Extended radiology coverage to level loads, signature pull demand 2) Process step disappears with voice recognition and systems that permit paperless process | Decrease RTT variation by 7% |
| Actual distribution 55 | Problem: Reports signed at beginning of shift, which amplifies "overnight" & "weekend" effect Solution: Electronic signature and distributive printing | Decrease RTT variation by 14% and decrease RTT mean by 150 minutes |

In the example shown in Table 3, the first key driver or indicator found was poor staffing that affected the time a patient had to wait for an available examination time, i.e., an opening. For example, a physician might order a procedure on a Tuesday morning but there may not be an opening until the following morning, causing a wait of about twenty-four hours. This wait is caused, in large part, by the single-shift staffing schedules of radiology departments. For example, if a department operates from 8 am to 4 pm, and all openings are booked for that period, an overnight delay is automatically added to the wait period because the next possible opening will occur the following day. By overlapping two shifts, e.g., 6 am to 2 pm and 12 pm to 8 pm the operating hours for the department are extended to 6 am to 8 pm increasing the number of possible openings in a single day and decreasing the likelihood of an overnight delay. Thus, one solution to reducing the time of the waiting for an opening step 27 is to overlap schedules.

The next key driver or indicator found through the regression analysis was batch processing. It was found that radiologists tend to wait until numerous images have accumulated before they are reviewed. Generally, an overnight delay occurred because radiologists reviewed images the day after they had been made. The same would occur at times when staffing levels were reduced, such as might occur on Saturdays and Sundays. These delays cause inefficiencies in transcription because transcribers face times of little activity followed by times where numerous dictated reports must be transcribed. By overlapping the schedule of radiologists, a more consistent stream of dictated reports is generated causing a more consistent production of transcriptions. The improvement is enhanced by matching transcription schedules to radiologist staffing.

Interestingly, it was found that batch behavior caused inefficiency in the printing and signature box steps 51 and 52. By effecting changes that cause more consistent production of work product, the RTT was reduced. Further, the results indicate that implementing electronic solutions such as voice-recognition and electronic distribution technologies are likely to eliminate the need for steps affected by batch processing. Thus, it is believed that further improvements in RTT may be made in hospitals and healthcare facilities that implement these technologies.

As can be seen above, the present invention provides a structured methodology for improving the efficiency of medical procedures and, more specifically, the production and distribution of radiological information. Various features and advantages of the invention are set forth in the following claims.

What is claimed is:

1. A method of evaluating inefficiencies in a procedure including a plurality of steps, the method comprising:
    collecting a plurality of characterization measurements, each characterization measurement corresponding to an one of the plurality of steps in the procedure;
    performing a sum of squares analysis on the collected characterization measurements;
    determining key drivers in at least some of the plurality of steps of the procedure; and
    performing a regression analysis on all of the key drivers.

2. A method as in claim 1, wherein the procedure is the production of a report in a department of a healthcare facility.

3. A method as in claim 2, wherein the department is a radiology department and the report is a radiology report.

4. A method as in claim 1, wherein the key drivers in each of the plurality of steps of the radiological procedure are determined.

5. A method as in claim 1, further comprising:
    determining a number of the plurality of steps having the highest percentage of contribution to the sum of squares prior to determining the key drivers of at least some of the plurality of steps of the procedure.

6. A method as in claim 1, further comprising modifying the key drivers.

7. A method as in claim 1, wherein the sum of squares analysis performed on the collected characterization measurements is an ANOVA analysis.

8. A method as in claim 1, wherein at least one characterization measurement is eliminated from the method prior to performing a sum of squares analysis.

9. A method as in claim 1, wherein a characterization measurement is added to the plurality of characterization measurements prior to performing the sum of squares analysis.

10. A method of evaluating inefficiencies in a radiological examination procedure having a plurality of steps, the method comprising:

collecting a plurality of characterization measurements, each characterization measurement corresponding to one of the plurality of steps in the radiological examination procedure;

performing a sum of squares analysis on the collected characterization measurements;

determining key drivers in at least some of the plurality of steps of the radiological examination process; and performing a regression analysis on at least some of the key drivers.

11. A method of evaluating inefficiencies in a radiological examination procedure as in claim 10, wherein the key drivers in each of the plurality of steps of the radiological examination procedure are determined.

12. A method of evaluating inefficiencies in a radiological examination procedure as in claim 10, further comprising:

determining a number of process steps having the highest percentage of contribution to the sum of squares prior to determining the key drivers of at least some of the plurality of steps of the radiological examination procedure.

13. A method of evaluating inefficiencies in a radiological examination procedure as in claim 10, further comprising modifying the key drivers.

14. A method of evaluating inefficiencies in a radiological examination procedure as in claim 10, wherein the procedure is the production of a report.

15. A method of evaluating inefficiencies in a radiological examination procedure as in claim 14, wherein one of the key drivers is the time required to distribute the report.

16. A method of evaluating inefficiencies in a radiological examination procedure as in claim 14, wherein one of the key drivers is the time to review and interpret a radiological image.

17. A method of evaluating inefficiencies in a radiological examination procedure as in claim 10, wherein the sum of squares analysis performed on the collected characterization measurements is an ANOVA analysis.

\* \* \* \* \*